(12) United States Patent
Koike et al.

(10) Patent No.: US 7,040,507 B2
(45) Date of Patent: May 9, 2006

(54) FOAM-TYPE HAIR DYE AND FOAM-TYPE HAIR DYE DISCHARGE CONTAINER

(75) Inventors: Kenzo Koike, Tokyo (JP); Keiji Sakamoto, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/379,688

(22) Filed: Mar. 6, 2003

(65) Prior Publication Data
US 2003/0192135 A1 Oct. 16, 2003

(30) Foreign Application Priority Data
Mar. 5, 2002 (JP) .............. 2002-058579
Apr. 12, 2002 (JP) .............. 2002-111273

(51) Int. Cl.
*B65D 35/22* (2006.01)
(52) U.S. Cl. .................. 222/94; 222/135; 222/190; 222/394; 222/402.1; 8/405
(58) Field of Classification Search ............... 222/190, 222/94, 95, 135, 394, 402.1; 8/405–406, 8/435, 611, 550, 554
See application file for complete search history.

(56) References Cited

U.S. PATENT DOCUMENTS

| | | | | |
|---|---|---|---|---|
| 3,669,321 A | * | 6/1972 | Susuki et al. | 222/402.24 |
| 3,709,437 A | * | 1/1973 | Wright | 239/343 |
| 3,804,302 A | * | 4/1974 | Yamada et al. | 222/182 |
| 3,849,659 A | * | 11/1974 | O'Keeffe | 250/492.1 |
| 4,860,933 A | * | 8/1989 | Morane et al. | 222/402.13 |
| 4,900,326 A | | 2/1990 | Grollier | |
| 4,985,955 A | * | 1/1991 | Grollier et al. | 8/406 |
| 5,021,067 A | * | 6/1991 | Grollier | 8/409 |
| 5,167,347 A | * | 12/1992 | Wiegner et al. | 222/94 |
| 5,288,494 A | | 2/1994 | Yoshihara et al. | |

FOREIGN PATENT DOCUMENTS

| | | |
|---|---|---|
| DE | 33 23 452 | 1/1985 |
| DE | 41 37 005 | 5/1993 |
| EP | 0 429 855 | 6/1991 |
| EP | 0 470 381 | 2/1992 |
| EP | 0 510 352 | 10/1992 |
| EP | 196 53 496 | 6/1997 |

(Continued)

OTHER PUBLICATIONS

Patent Abstracts of Japan, JP 04-131154, May 1, 1992.

*Primary Examiner*—Frederick C. Nicolas
(74) *Attorney, Agent, or Firm*—Oblon, Spivak, McClelland, Maier & Neustadt, P.C.

(57) ABSTRACT

A foam-type hair dye apparatus, has a container main body in which liquid hair dye containing a dye, surfactant, and thickener is stored; at least one jetting orifice for jetting the liquid hair dye from the container main body; and a liquid reservoir member disposed opposite the jetting orifice. The jet flow of liquid hair dye from the jetting orifice is blended with air from outside the container and transformed into foam-type hair dye in the liquid reservoir member. A foam-type hair dye discharge apparatus according to another embodiment uses a double aerosol container including an inner bag filled with undiluted solution; an outer container disposed on the external side of the inner bag and filled with compressed gas in the space between the outer container and the inner bag; and a valve mechanism.

14 Claims, 6 Drawing Sheets

FOREIGN PATENT DOCUMENTS

| | | |
|---|---|---|
| EP | 0 887 067 | 12/1998 |
| EP | 0 994 042 | 4/2000 |
| FR | 2 765 112 | 12/1998 |
| GB | 1 601 238 | 10/1981 |
| JP | 2002-66388 | 3/2002 |
| WO | WO 00/72821 | 12/2000 |
| WO | WO 03/033166 | 4/2003 |

* cited by examiner

FIG. 1A
FIG. 1B
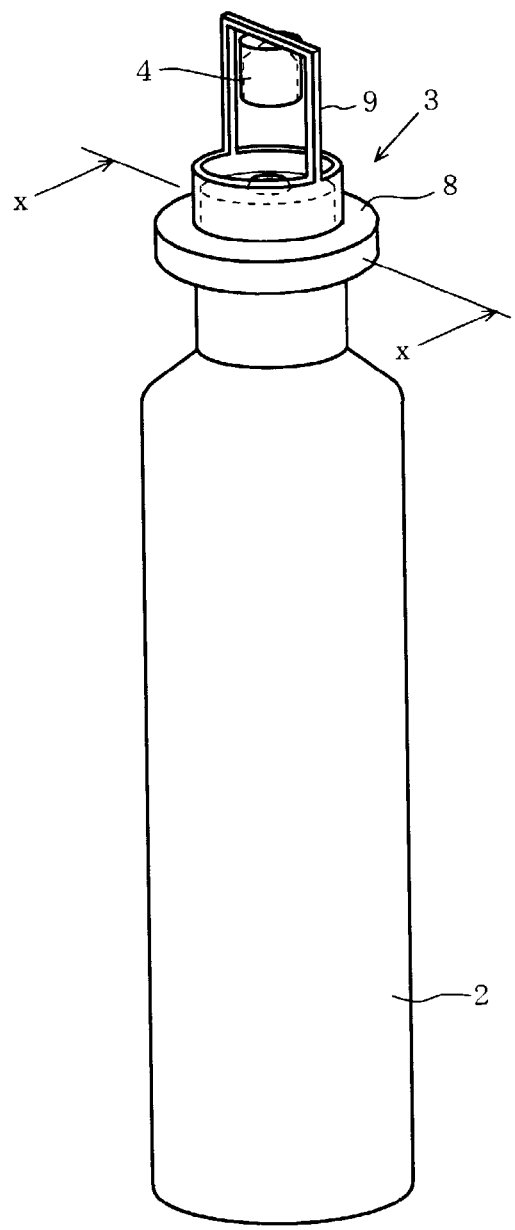
1A
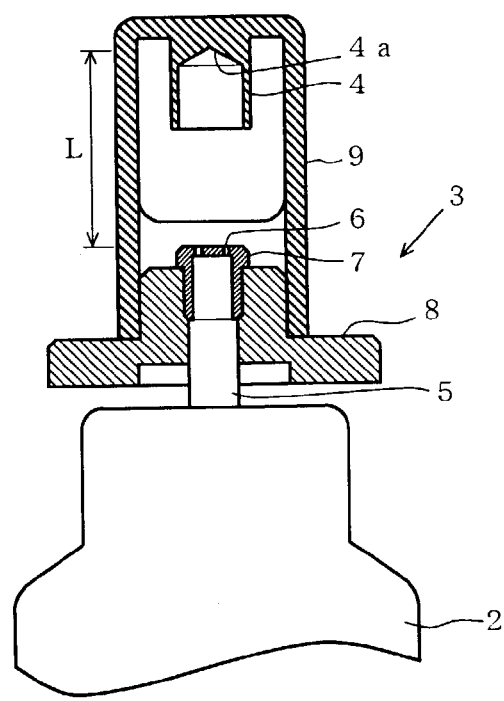
(x — x sectional view)

1A (x—x sectional view)

(x – x sectional view)

FOAM-TYPE HAIR DYE AND FOAM-TYPE HAIR DYE DISCHARGE CONTAINER

BACKGROUND OF THE INVENTION

1. Field of the Invention

The present invention relates to a foam-type hair dye which is converted to foam by the blending of gas (air from outside the container, or compressed gas from inside of the container, for example) during use, to an application method for foam-type hair dye, and to a foam-type hair dye discharge apparatus.

2. Related Art of the Invention

In conventional practice, foam-type hair dye is used because of handling considerations related to minimal fluid dripping and the ease of achieving thin and even application.

Examples of discharge apparatuses for foam-type hair dye include hand foamers in which a liquid hair dye is stored in a container at normal pressure and is discharged from a discharge nozzle provided with a mesh using a pump mechanism, and devices for discharging liquid hair dye from a nozzle provided with a mesh using a squeeze container. There are also devices which use aerosol containers wherein LPG, nitrogen gas, or another propellant is stored together with liquid hair dye in a pressure-resistant container, and is then released.

However, conventional foam-type hair dye discharge apparatuses that use a normal-pressure container have a drawback in that agents unstable with regard to air cannot be stored over a long period of time, and cannot be used in air oxidation hair dyes in particular. Because foam is difficult to form in a hand foamer or other normal-pressure container when the liquid hair dye has high viscosity, the viscosity of the liquid hair dye is normally set to 100 mPa·s or less, resulting in fluid dripping, prolonged discharge time, and other drawbacks.

There are other problems in foam-type hair dye discharge apparatuses that use aerosol containers in that there are restrictions in the combination of propellants and liquid hair dye, the specific volume of the foam (foam-type hair dye volume/foam-type hair dye weight) is commonly high at 10 mL/g or more, and application is difficult.

SUMMARY OF THE INVENTION

A first object of the present invention is to convert liquid hair dye into foam with a novel mechanism, to allow application to hair with good handling characteristics, and to improve the shelf life of liquid hair dye.

A second object of the present invention is to provide a foam-type hair dye discharge apparatus that resolves the shelf life problem of agents when a normal pressure container is used, and resolves the restrictions in the combination of propellants and liquid hair dye when an aerosol container is used, thereby allowing liquid hair dye containing air oxidation dye to be discharged with compressed air and converted to foam, and permitting the use of a novel aerosol container which does not allow deterioration of the shelf life of the hair dye.

The present inventors discovered that an arbitrary hair dye is capable of being stably stored over a long period of time, that the handling characteristics during use can be improved, and that the first object described above can be achieved by sealing off the liquid hair dye from outside air during storage and by blending gas (air from outside the container, or compressed gas from inside of the container, for example) during use to convert the liquid hair dye into foam with a particular specific volume.

The present inventors further discovered that when an inner bag of a double container comprising an inner bag and outer bag is filled with undiluted solution, the space between the inner and outer containers is filled with compressed gas, and the compressed gas is jetted simultaneously with the undiluted solution, the undiluted solution can be converted to foam by the compressed gas jetted simultaneously with the undiluted solution, and the undiluted solution and the compressed gas are separately stored, making it possible to prevent the storage stability of the undiluted solution from being adversely affected by the compressed gas, and hence allowing the second object described above to be achieved by filling the inner bag of this type of double container with liquid hair dye as the undiluted solution.

In other words, the present invention provides a foam-type hair dye comprising a liquid hair dye that contains dyes, surfactants, and thickeners, and a gas (air from outside the container, or compressed gas from inside of the container, for example) that is blended into jet flow of the liquid hair dye, wherein the specific volume of the foam is 1.2 to 5 mL/g.

The present invention further provides an application method for foam-type hair dye comprising blending air from outside the container with the jet flow of liquid hair dye by jetting liquid hair dye containing a dye, surfactant, and thickener from one or a plurality of jetting orifices of a discharge container to a liquid reservoir member disposed opposite the jetting orifices; forming a foam-type hair dye in the liquid reservoir member; and applying the foam-type hair dye to hair.

The present invention furthermore provides a foam-type hair dye apparatus comprising a container main body wherein liquid hair dye containing a dye, surfactant, and thickener is stored, one or a plurality of jetting orifices for jetting the liquid hair dye from the container main body, and a liquid reservoir member disposed opposite the jetting orifices, wherein the hair dye discharge apparatus blends air from outside the container with the jet flow of liquid hair dye jetted from the jetting orifices toward the liquid reservoir member, and forms foam-type hair dye in the liquid reservoir member.

As a foam-type hair dye discharge apparatus according to a different embodiment from the foam-type hair dye discharge apparatus described above, the present invention also provides a foam-type hair dye discharge apparatus composed of a double aerosol container comprising an inner bag filled with undiluted solution; an outer container disposed on the external side of the inner bag and filled with compressed gas in the space defined between the outer container and the inner bag; and a valve mechanism for allowing the undiluted solution stored in the inner bag to be jetted by the pressure of the compressed gas, jetting the compressed gas, mixing the undiluted solution and the compressed gas, and discharging the product in foam form, wherein the foam-type hair dye discharge apparatus is filled with liquid hair dye as the undiluted solution. As a double aerosol container suitable for this foam-type hair dye discharge apparatus, the present invention also provides a double aerosol container comprising an inner bag filled with undiluted solution; an outer container disposed on the external side of the inner bag and filled with compressed gas in the space defined between the outer container and the inner bag; and a valve mechanism for allowing the undiluted solution stored in the inner bag to be jetted by the pressure of the compressed gas, jetting the compressed gas, mixing the undiluted solution and the compressed gas, and discharging the product in foam form.

BRIEF DESCRIPTION OF THE DRAWINGS

FIG. 1A is a perspective view of an embodiment of the foam-type hair dye discharge apparatus of the present invention, and FIG. 1B is a cross-sectional view of the vicinity of the jetting orifice thereof;

DETAILED DESCRIPTION OF THE INVENTION

Figure 2:
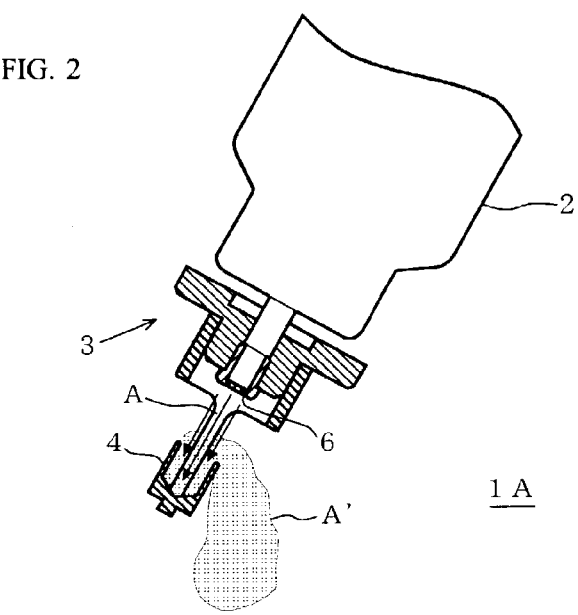
FIG. 2 is a descriptive view of the foam-type hair dye discharge apparatus of the present invention during use.

The present invention is described in detail below with reference to the diagrams. It should be noted that the same symbols in each diagram represent identical or equivalent constituent elements.

FIG. 1A is a perspective view of the foam-type hair dye discharge apparatus 1A of the present invention, and FIG. 1B is a cross-sectional view of the vicinity of the jetting orifice thereof.

This foam-type hair dye discharge apparatus 1A comprises a pressure-resistant container main body 2 wherein liquid hair dye is stored, a valve 3 disposed in the upper portion of the container main body 2, and a liquid reservoir member 4 further disposed thereabove.

Valve 3 comprises a stem 5 linking the interior and exterior of the container main body 2 by being pressed toward the container main body 2 side, a nozzle 7 set on top of stem 5 and provided with an jetting orifice 6 at the leading edge thereof, and a valve base 8 disposed around the circumference of the upper edge portion of the stem 5. Here, the jetting orifice 6 in not limited to one, but may be a plurality.

The diameter, quantity, and placement of the jetting orifice 6 are determined according to the viscosity, flowability, and other properties of the liquid hair dye within a range in which air can be being blended into the liquid hair dye. When there is only one jetting orifice 6, for example, and the viscosity of the liquid hair dye is 400 to 50,000 mPa·s (25° C., B-type viscometer), the diameter of the jetting orifice 6 is set to 0.4 to 0.6 mm; the discharge velocity of the liquid hair dye is set to 0.1 to 100 g/sec, but preferably 1 to 30 g/sec; the initial linear velocity immediately after discharge is set to 0.1 to 500 m/sec, but preferably 1 to 100 m/sec, and the linear velocity at time of impact when the jetted liquid hair dye strikes the bottom portion 4a of the liquid reservoir member is set to 0.1 to 300 m/sec, but preferably 1 to 50 m/sec. Air from outside the container is thereby blended with the liquid hair dye jetted from the jetting orifice 6 so that the specific volume of the foam is 1.2 to 5 mL/g, but preferably 1.3 to 3 mL/g, forming foam-type hair dye.

To generate foam, air inside the container is taken into the foam and converted to the internal gas of the foam in conventional hand foamers, and LPG or another propellant inside the container becomes the internal gas of the foam in conventional aerosol containers, but the foam-type hair dye discharge apparatus 1A differs in that air outside the container is blended. Conventional hand foamers and aerosol containers have a drawback whereby the specific volume of the foam is commonly high (10 mL/g or more), and the time required for hair dyeing is prolonged when this foam is used as a hair dye. There is a further problem in that the net application quantity is small when the same volume of hair dye is used, but the foam-type hair dye discharge apparatus of the present invention has advantages in that the specific volume of the foam is low in comparison with conventional examples, the hair dyeing time is shortened, and the net application quantity can be increased.

The liquid reservoir member 4 has a bottomed cylindrical configuration with an opening to the jetting orifice 6, and the bottom portion 4a and jetting orifice 6 are held by the liquid reservoir member holding portion 9 at a predetermined distance L. The liquid reservoir member holding portion 9 is integrally formed with the liquid reservoir member 4, and affixed to the valve base 8.

From a handling and foaming properties, the distance L between the bottom portion 4a of the liquid reservoir member and the jetting orifice 6 is preferably kept at 5 to 50 mm, and more preferably at 10 to 30 mm.

The liquid hair dye stored in the container main body 2 contains dyes, surfactants, and thickeners. Propellants are also filled into the container main body 2 together with liquid hair dye.

Examples of dyes contained in the liquid hair dye include indoline derivatives, indole derivatives, and other air oxidation dyes that can be auto-oxidized by air; enzymes having oxidation capability; oxidation dye intermediates that are oxidation-polymerized by the enzymes thereof; p-phenylenediamine, toluene-2,5-diamine, and other oxidation-type dyes, and direct dyes, pyrogallol, and other non-oxidation type dyes, which are used singly or as mixtures.

The dye content of the liquid hair dye depends on the type of dye or the like and may, for example, be 0.01 to 5 wt %, with 0.1 to 4 wt % being particularly preferred, in the case of oxidation-type dyes, and 0.001 to 5 wt %, with 0.01 to 4 wt % being particularly preferred, in the case of direct dyes.

Surfactants are added as foaming agents and/or homogenizing agents. Examples of such surfactants include polyoxyethylene oleyl ether, polyoxyethylene stearyl ether, and other polyoxyethylene alkyl ethers; polyoxyethylene nonylphenyl ether, polyoxyethylene octylphenyl ether, and other polyoxyethylene alkylphenyl ethers; and polyoxyethylene sorbitan fatty acid esters, fatty acid alkylolamides, polyoxyethylene-sec-tetradecyl ether, and other nonionic surfactants. Anionic, cationic, and amphoteric surfactants may also be used. The surfactant content of the liquid hair dye depends on the surfactant, the type of dye used, and the like, and may, for example, be set to 0.01 to 5 wt % in the case of a nonionic surfactant.

Thickeners are admixed in order to adjust the viscosity of the liquid hair dye to 100 to 100,000 mPa·s (25° C., B-type viscometer) with the aim of preventing the foam-type hair dye applied to the hair from dripping. Examples of suitable thickeners include hydroxyethyl cellulose, ethers of hydroxyethyl cellulose and glycidyl trimethylammonium chloride, methyl cellulose, carboxymethyl cellulose, and other cellulose derivatives; xanthan gum, guar gum, and other natural gums; and polyvinyl pyrrolidone, crosslinked polyacrylic acid or salts thereof, polyacrylic acid or salts thereof, polyacrylamide, and other synthetic polymers. The thickener content of the liquid hair dye depends on the thickener, the type of dye used, or the like, and may, for example, be set to 0.01 to 5 wt %, in the case of xanthan gum.

In addition, pH conditioners, antioxidants, stabilizers, buffers, chelating agents, solubilizing agents, preservatives, perfumes, tactile improvers, and other materials may be added.

Examples of propellants that may be used include nitrogen gas, carbon dioxide, argon gas, and other compressed gases, as well as liquefied petroleum gas, lower saturated hydrocarbons, dimethyl ether, and other liquefied gases.

As an example of a method of use of the foam-type hair dye discharge apparatus 1A, the container main body 2 is turned upside down as shown in FIG. 2. Jetting of the propellant alone from the jetting orifice 6 is thereby prevented when the valve 3 is pressed in the direction toward the container main body 2. The valve 3 is subsequently pressed toward the container main body 2. Liquid hair dye A is thereby jetted from the jetting orifice 6 and caused to strike the liquid reservoir member 4. Air from outside the container is blended into the jet flow of the liquid hair dye A in the period after the jetting from the jetting orifice 6 until the impact on the liquid reservoir member 4. The liquid hair dye A with blended air strikes the liquid reservoir member 4, and then the liquid hair dye A becomes foam through intense mixing of the liquid hair dye A and the air, and flows down from the liquid reservoir member 4. The foam-type hair dye A' thus obtained can be applied to hair using a comb or other means.

Thus, using the foam-type hair dye discharge apparatus 1A allows the liquid hair dye to be isolated from air outside the container and sealed inside the container main body 2 during storage thereof, making it possible to ensure better storage stability even when the liquid hair dye contains an air-oxidation dye. Because the liquid hair dye becomes foam through the blending of air from outside the container during use, coloring through air oxidation of the liquid hair dye can be facilitated when the liquid hair dye contains an air-oxidation dye. Regardless of whether the liquid hair dye contains an air-oxidation dye or not, the hair dye is easily and thinly applied to the hair without any waste or unevenness by conversion of the liquid hair dye to foam, and the handling characteristics of the hair dye are greatly improved because the dripping is minimal during application.

Figure 3A:
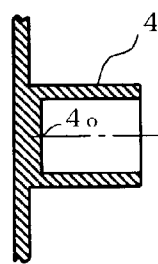
FIG. 3A is a cross-sectional view of a variation of the liquid reservoir member.
Figure 3B:
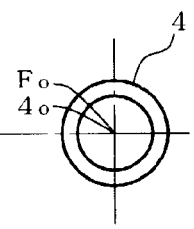
FIG. 3B is a top view thereof.
Figure 3C:
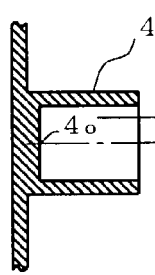
FIG. 3C is a cross-sectional view of another variation of the liquid reservoir member.
Figure 3D:
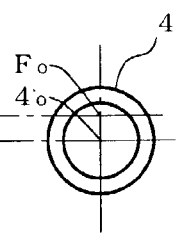
FIG. 3D is a top view thereof.
Figure 3E:
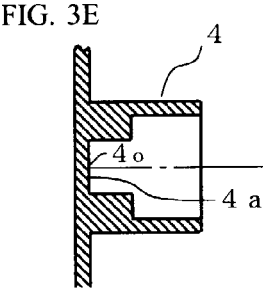
FIG. 3E is a cross-sectional view of yet another variation of the liquid reservoir member.
Figure 3F:
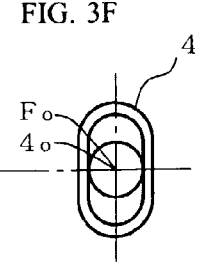
FIG. 3F is a top view thereof.

The foam-type hair dye discharge apparatus 1A may have a variety of other aspects. The shape of the liquid reservoir member 4 and the placement of the liquid reservoir member 4 with regard to the jetting orifice 6 may be appropriately adjusted because the air content of the foam-type hair dye that flows down from the liquid reservoir member 4 varies depending on these factors. More specifically, the center 4o of the bottom portion of the liquid reservoir member 4 may be set to match the center Fo of the jet flow when the member has a bottomed cylindrical configuration as shown in FIGS. 3A and 3B, the center 4o of the bottom portion of the liquid reservoir member 4 may be offset from the center Fo of the jet flow as shown in FIGS. 3C and 3D, or a step may be provided to the bottom portion 4a of the liquid reservoir member 4, as shown in FIGS. 3E and 3F. When a plurality of jetting orifices 6 are provided, these embodiments may occur in combination.

In the same manner as in a known aerosol container with a double container, the container main body 2 may be configured as a double container comprising an outer container and an inner bag, with the inner bag filled with liquid hair dye, and propellant filled between the outer container and the inner bag. Because jetting of the propellant alone from the jetting orifice 6 is thereby prevented when the system is used upright or the like, the foam-type hair dye discharge apparatus can be used facing any direction.

Figure 4A:
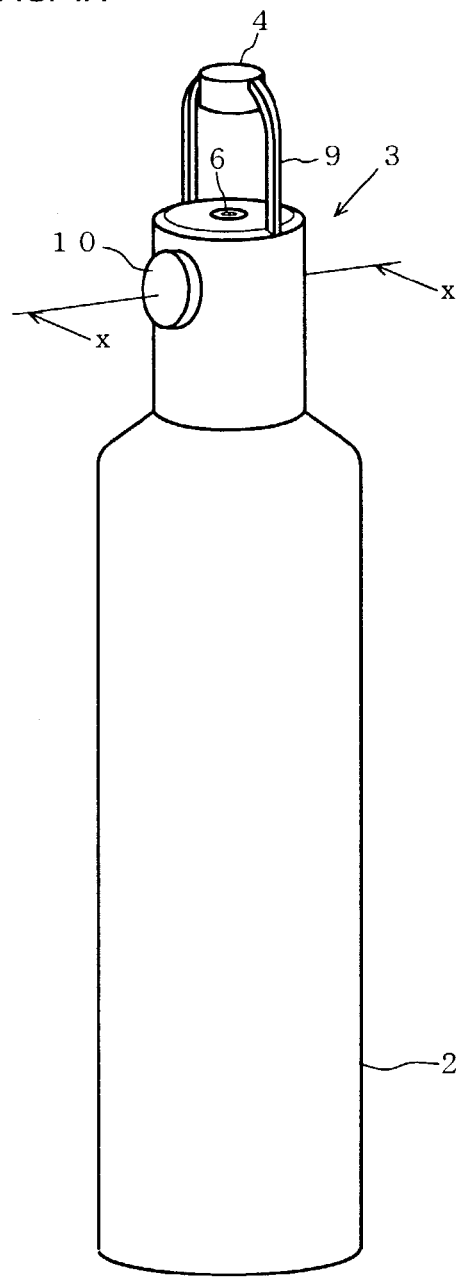
FIG. 4A is a perspective view of another embodiment of the foam-type hair dye discharge apparatus of the present invention.
Figure 4B:
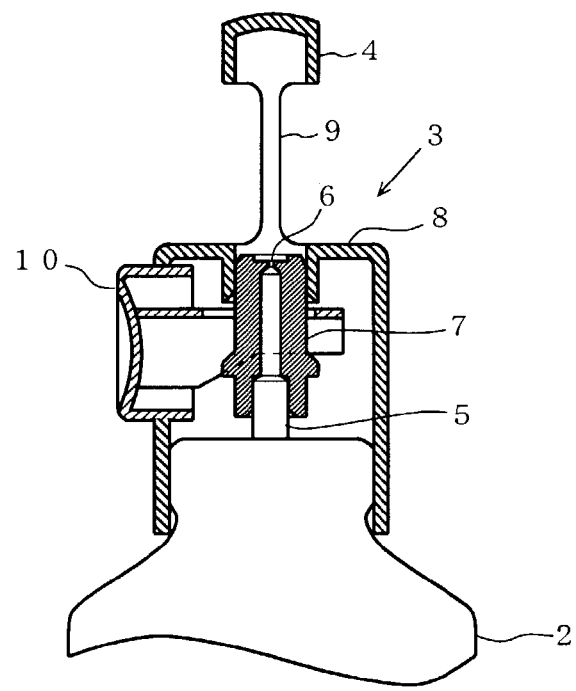
FIG. 4B is a cross-sectional view of the vicinity of the jetting orifice thereof.

FIG. 4A is a perspective view of the foam-type hair dye discharge apparatus 1B according to another embodiment of the present invention, and FIG. 4B is a cross-sectional view of the vicinity of the jetting orifice thereof. The foam-type hair dye discharge apparatus 1B is configured so that pressing a button 10 disposed on the lateral surface of the valve 3 causes a nozzle 7 and a stem 5 linked to the nozzle 7 to be pressed toward the container main body 2, and liquid hair dye to be jetted from the jetting orifice 6. Excepting this, the configuration is identical to the foam-type hair dye discharge apparatus 1A of FIG. 1A.

Figure 5A:
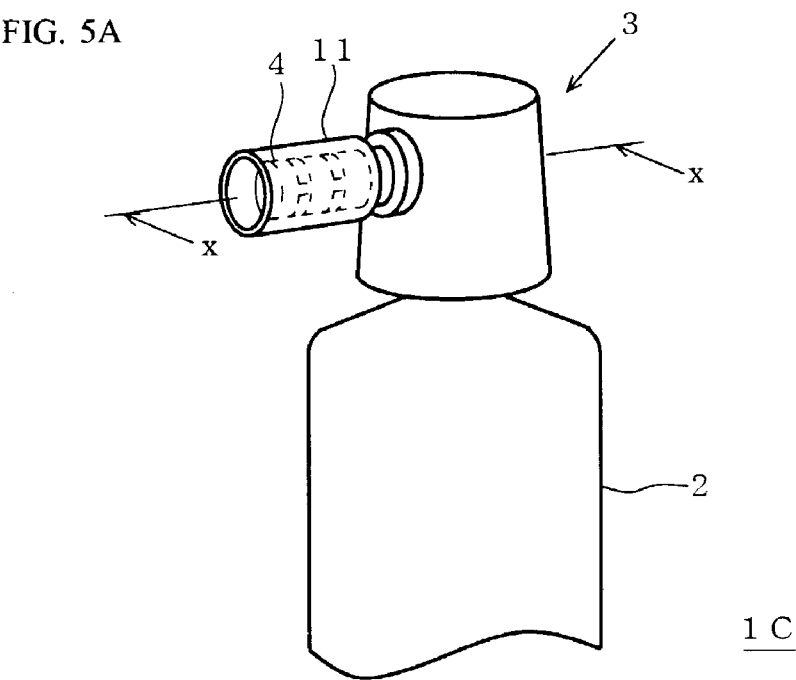
FIG. 5A is a perspective view of the vicinity of the jetting orifice of yet another embodiment of the foam-type hair dye discharge apparatus of the present invention.
Figure 5B:
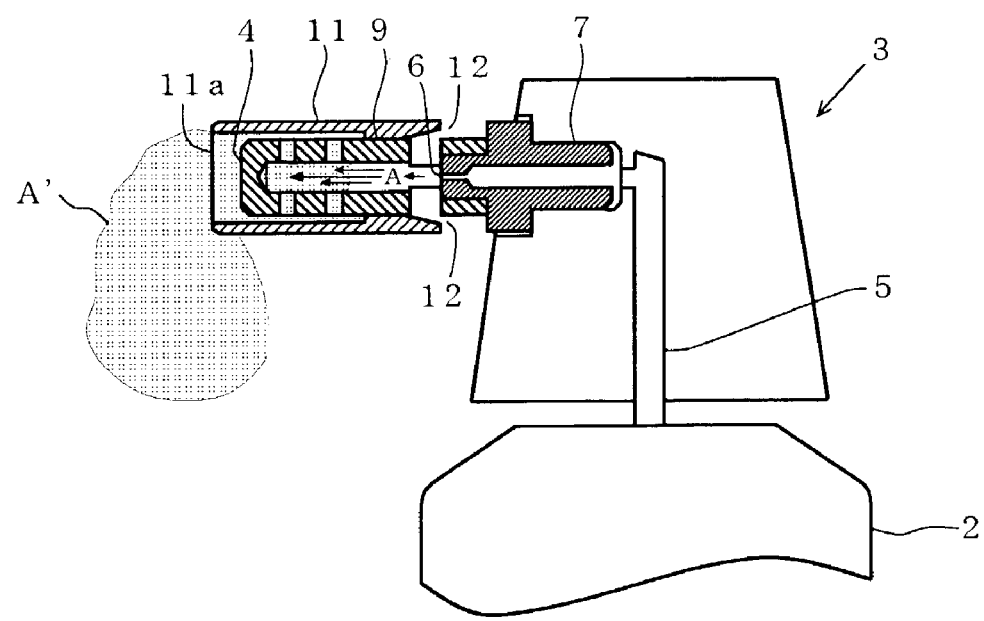
FIG. 5B is a cross-sectional view thereof.

FIG. 5A is a perspective view of the vicinity of the jetting orifice of a foam-type hair dye discharge apparatus 1C according to yet another embodiment, and FIG. 5B is a cross-sectional view thereof. In this foam-type hair dye discharge apparatus 1C, the nozzle 7 is disposed perpendicular to the stem 5, and a cylindrical external sheath material 11 is disposed adjacent to the outside of the liquid reservoir material 4. The external sheath material 11 is affixed to the liquid reservoir member holding portion 9 in a position away from the jetting orifice 6 so as to allow for an air intake port 12 to be secured.

When the valve 3 is pressed toward the container main body 2 during the use of the foam-type hair dye discharge apparatus 1C, the liquid hair dye A is jetted from the jetting orifice 6 in the direction perpendicular to the stem 5, the jet flow thereof strikes the liquid reservoir member 4 while being blended with air supplied from the air intake port 12, and the foam-type hair dye A' formed thereby flows down from the end portion 11a of the external sheath material 11 on the opposite side from the jetting orifice 6. Thus, the foam-type hair dye discharge apparatus is easier to use because the foam-type hair dye discharge apparatus 1C allows the downflow direction of the foam-type hair dye A' to be aligned in the direction toward the end portion 11a of the external sheath material.

The foam-type hair dye of the present invention can be obtained by mixing the liquid hair dye and air with the aid of the foam-type hair dye discharge apparatus described above, but may also be obtained by blending gas (air from outside the container, or compressed gas from inside of the container, for example) into the jet flow of the liquid hair dye by jetting liquid hair dye in any container, and mixing the gas with the liquid hair dye.

The application method of the hair dye of the present invention can be easily performed by using the foam-type hair dye discharge apparatus described above, but can also be easily performed by forming a liquid hair dye jet flow with a squeeze container, and blending the jet flow with external air.

A double aerosol container particularly suitable for a foam-type hair dye discharge apparatus of a differing aspect from the foam-type hair dye discharge apparatus described up to this point is subsequently described with reference to the FIGS. 6A, 6B, and 7. It should be noted that the same symbols in each diagram represent identical or equivalent constituent elements.

Figure 6A:
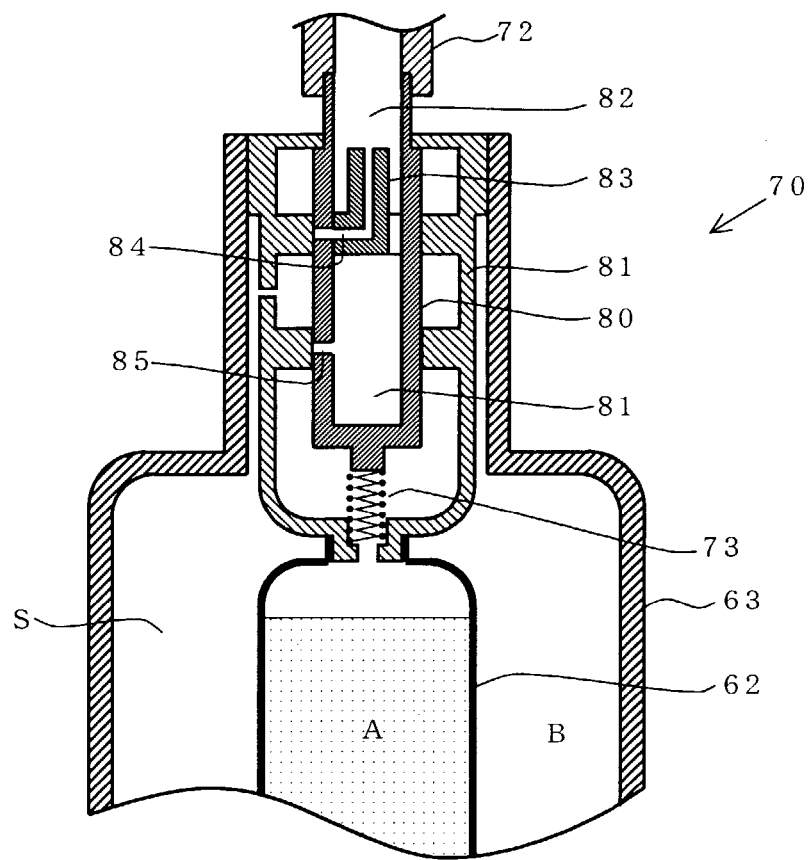
FIGS. 6A and B are cross-sectional views of the valve mechanism of the double aerosol container suitable in another embodiment of the foam-type hair dye discharge apparatus of the present invention.
Figure 6B:
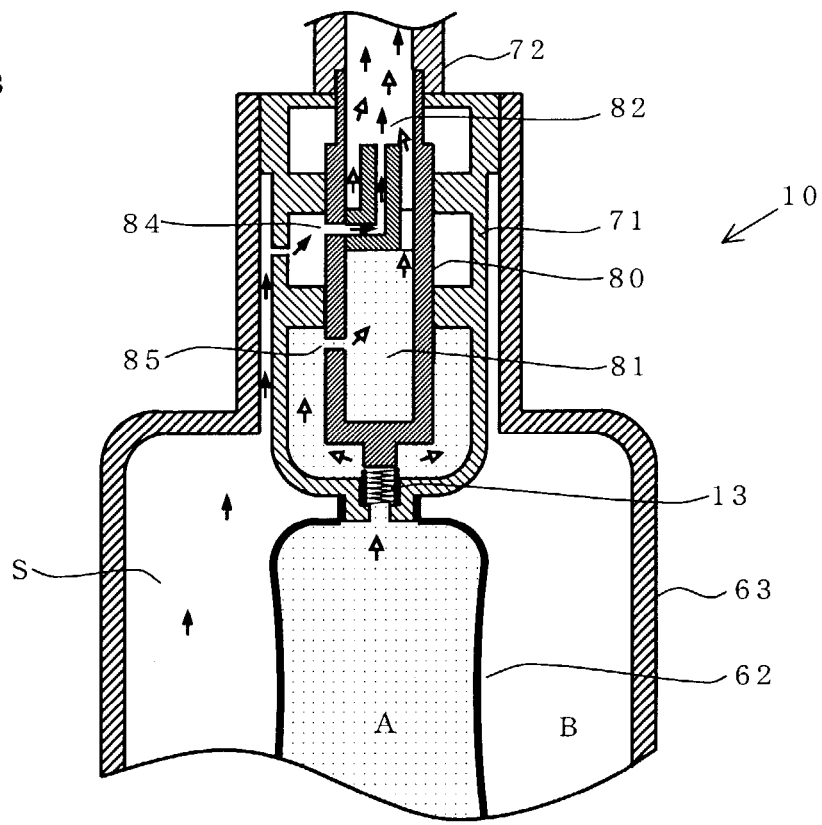
Figure 7:
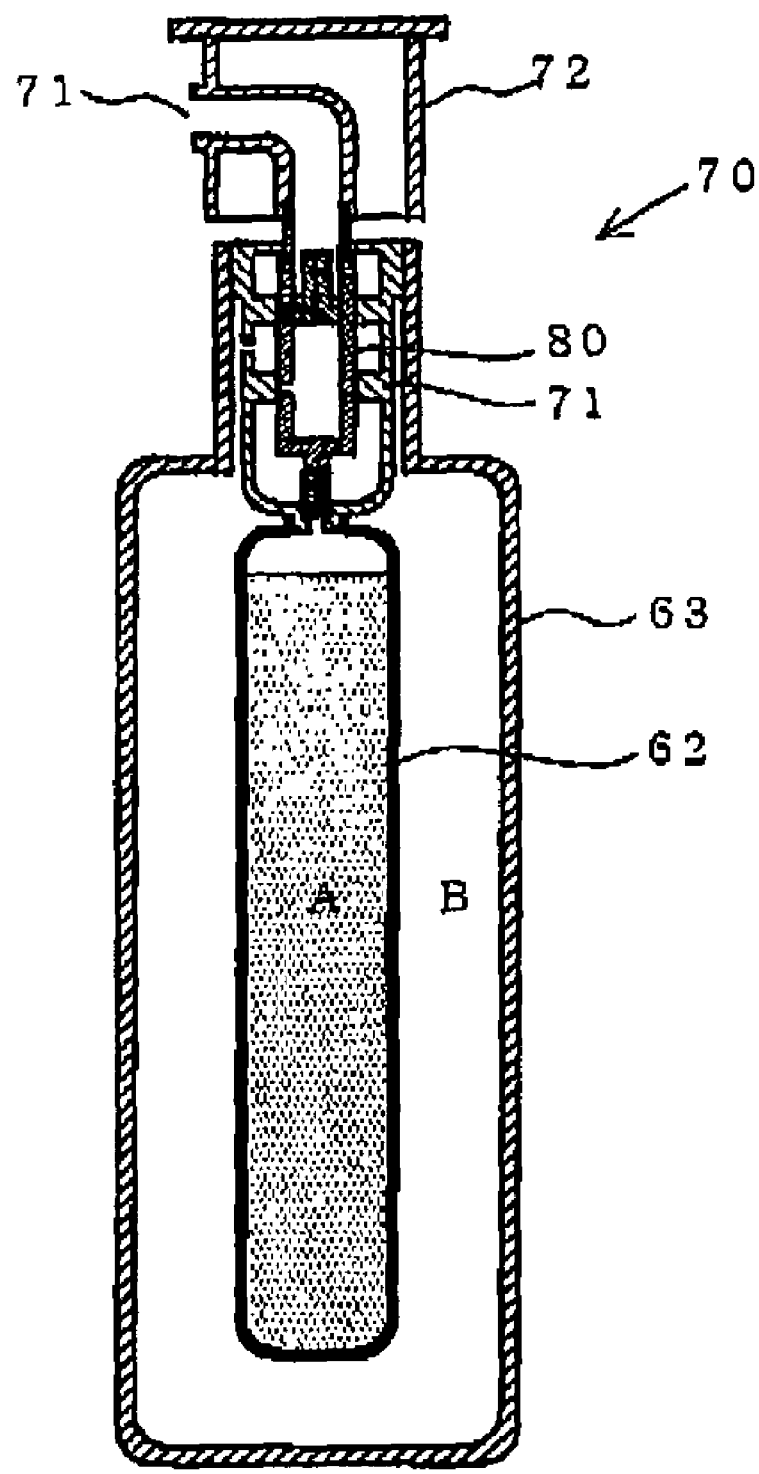
FIG. 7 is a conceptual cross-sectional view thereof.

FIG. 7 is a conceptual cross-sectional view of the double aerosol container 61, FIGS. 6A and 6B are cross-sectional views that illustrate the valve mechanism thereof, FIG. 6A shows the stem in an non-pressed state, and FIG. 6B shows the stem in a pressed state.

This aerosol container 61 comprises an inner bag 62 filled with undiluted solution A, an outer container 63 disposed on the outside of the inner bag 62, and a valve mechanism 70.

The outer container 63 is formed from metal material or the like, and air, oxygen gas, nitrogen gas, carbon dioxide, argon gas, or any other compressed gas B is filled between the outer container 63 and inner bag 62. The fill pressure of the compressed gas B is preferably set to 0.3 to 1.0 MPa from the perspective of stably discharging undiluted solution until the end.

The inner bag 62 is soft and flexible, and is formed from at least a synthetic resin or other material essentially impermeable to the components of the compressed gas B, which are not intended to be mixed with the undiluted solution A during storage.

The valve mechanism 70 comprises a housing 71, a stem 80 that moves up and down inside the housing 71, an actuator 72 disposed on the upper end portion of the stem 80, and a spring 73 disposed between the lower end portion of stem 80 and the housing 71, providing outward force to the stem 80 pressed into the interior of the container.

An internal piece 83 that separates the liquid flow path 81 on the internal side of the container and the gas-liquid mixture flow path 82 on the external side thereof, is fixed to the inside of the stem 80, and a gas supply hole 84, disposed in the peripheral wall of the internal piece 83 and stem 80, links the space S between the outer container 63 and the inner bag 62 and the gas-liquid mixture flow path 82 inside the stem 80 when stem 80 is pressed into the interior of the container, as shown in FIG. 6B. A liquid supply hole 85, disposed in the peripheral wall of the stem 80, links the interior of the inner bag 62 and the liquid flow path 81 inside the stem 80 when stem 80 is pressed into the interior of the container, as shown in the same diagram. With the stem 80 not pressed into the interior of the container, as shown in FIG. 6A, these gas supply holes 84 and liquid supply holes 85 in the peripheral wall of the stem 80 are closed off by the wall surface of the housing 71, and the interior of the inner bag 62 and the space S between the outer container 63 and the inner bag 62 are each independently sealed.

This double aerosol container 61 operates as follows. First, with the stem not pressed as in FIG. 6A, the undiluted solution A filled into the interior of the inner bag 62 and the compressed gas B filled into the space S between the outer container 63 and the inner bag 62 are each sealed and stored. Consequently, it is possible to prevent the undesirable reduction in the shelf life of the undiluted solution A due to the mixing of the undiluted solution A and the compressed gas B.

When the actuator 72 is pressed down and the stem 80 is pressed into the interior of the container, the interior of the inner bag 62 and the liquid flow path 81 inside the stem 80 become linked by way of the liquid supply hole 85, and the undiluted solution A filled into the inner bag 62 passes through the liquid supply hole 85 and the liquid flow path 81, and is jetted into the gas-liquid mixture flow path 82 by the pressure of the compressed gas B. The gas-liquid mixture flow path 82 in the stem 80 and the space S between the outer container 63 and the inner bag 62 are linked at this time by way of the gas supply hole 84, and the compressed gas B is jetted into the gas-liquid mixture flow path 82. The undiluted solution A and the compressed gas B are therefore mixed in the gas-liquid mixture flow path 82, and the resulting mixture is discharged in foam form from the discharge port 74 on the actuator 72.

The double aerosol container 61 is not particularly limited in terms of application and can be widely used for discharging a foam obtained by mixing undiluted solution A and compressed gas B. In particular, storing undiluted solution A and compressed gas B in mixed form is not possible because these react, but favorable application is obtained when these are mixed and discharged during use. In a specific example of application of the foam-type hair dye discharge apparatus, the inner bag 62 is filled with liquid hair dye, the space S between the outer container 63 and the inner bag 62 is filled with compressed gas, and foam-type hair dye is discharged by the jetted liquid hair dye and the compressed gas, as described above.

When the double aerosol container shown in FIGS. 6A, 6B, and 7 is used as a foam-type hair dye discharge apparatus, the inner bag is filled with liquid hair dye. Examples of dyes contained in the liquid hair dye, each of which may be used alone or in a mixture, include indoline derivatives, indole derivatives, and other air oxidation dyes that are auto-oxidized by air; oxidation dye intermediates that are oxidation-polymerized by enzymes having oxidation capability and enzymes thereof, toluenediamine and other oxidation-type dyes; and direct dyes, pyrogallol, and other non-oxidation type dyes. In particular, hair dye is preferably discharged in a foam form using a solution that contains an air-oxidation dye as a liquid hair dye, and using compressed air as a compressed gas, because the contact area between the air-oxidation dye and the air can be increased in comparison with discharging hair dye in a foam form using conventional LPG, nitrogen gas, or other propellant, resulting in greater dyeing performance.

The dye content of the liquid hair dye depends on the type of dye or the like and may, for example, be 0.01 to 5 wt %, with 0.1 to 4 wt % being particularly preferred, in the case of oxidation-type dyes, and 0.001 to 5 wt %, with 0.01 to 4 wt % being particularly preferred, in the case of direct dyes.

Surfactants may be added as foam stabilizing agents and/or homogenizing agents, and thickeners are preferably added as viscosity modifiers.

Examples of such surfactants include polyoxyethylene oleyl ether, polyoxyethylene stearyl ether, and other polyoxyethylene alkyl ethers; polyoxyethylene nonylphenyl ether, polyoxyethylene octylphenyl ether, and other polyoxyethylene alkylphenyl ethers; and polyoxyethylene sorbitan fatty acid esters, fatty acid alkylolamides, polyoxyethylene-sec-tetradecyl ether, and other nonionic surfactants. Anionic, cationic, and amphoteric surfactants may also be used. The surfactant content of the liquid hair dye depends on the surfactant, the type of dye used, and the like, and may, for example, be set to 0.01 to 5 wt % in the case of a nonionic surfactant.

Examples of suitable thickeners include hydroxyethyl cellulose, ethers of hydroxyethyl cellulose and glycidyl trimethylammonium chloride, methyl cellulose, carboxymethyl cellulose, and other cellulose derivatives; xanthan gum, guar gum, and other natural gums; and polyvinyl pyrrolidone, crosslinked polyacrylic acid or salts thereof, polyacrylic acid or salts thereof, polyacrylamide, and other synthetic polymers. The thickener content of the liquid hair dye depends on the thickener, the type of dye used, or the like, and may, for example, be set to 0.01 to 5 wt %, in the case of xanthan gum.

In addition, pH conditioners, antioxidants, stabilizers, buffers, chelating agents, solubilizing agents, preservatives, perfumes, tactile improvers, and other materials may be added.

When a double aerosol container is used to discharge foam-type hair dye, the specific volume of the foam-type hair dye (foam-type hair dye volume/foam-type hair dye weight) can be adjusted over a wide range, such as 1 to 50 mL/g, by suitably setting the ratio of the hole diameter of the liquid supply hole 85 as the jetting orifice for the liquid hair dye and the hole diameter of the gas supply hole 84 as the jetting orifice for the compressed gas, but is preferably adjusted to 1.2 to 5 mL/g, and more preferably 1.3 to 3 mL/g.

The double aerosol container shown in FIGS. 6A, 6B, and 7 may also be used as a foam-type hair dye application container when known comb-type objects are attached to the discharge port thereof.

With this double aerosol container, undiluted solution and compressed gas for jetting the undiluted solution foam are individually sealed and stored, the compressed gas is jetted during the jetting of the undiluted solution, and these components are mixed and discharged in foam form.

This double aerosol container is therefore useful in cases where undiluted solution and compressed gas cannot be stored in mixed form. In particular, when a liquid hair dye containing an air-oxidation dye is filled as an undiluted solution, and compressed air is used as compressed gas, good dyeing performance can be achieved because the air-oxidation dye and air are discharged as an adequately mixed foam.

EXAMPLES

Example 1

(1) Preparation of Liquid Hair Dye and Manufacture of Foam-Type Hair Dye Discharge Apparatus Liquid hair dyes A and B containing an oxidation dye intermediate were prepared by measuring and mixing each ingredient according to the formula shown in Table 1. The viscosities of the liquid hair dyes A and B were 800 mPa·s and 12,000 mPa·s (B-type viscometer, No. 2 rotor, 25° C.), respectively.

Next, 100 g of the resulting hair dye were introduced into the container main body (volume: about 0.2 L) of the foam-type hair dye discharge apparatus 1A of FIG. 1A, the system was clinched and degassed, propellant (nitrogen) was added to achieve an internal pressure (gage pressure) of about 8 MPa, and a foam-type hair dye discharge apparatus was obtained. Three types of foam-type hair dye discharge apparatuses were fabricated in this case, with hole diameters of 0.4 mm, 0.5 mm, and 0.6 mm for the jetting orifice 6.

TABLE 1

| Ingredients | Liquid hair dye A | Liquid hair dye B |
|---|---|---|
| Toluene-2,5-diamine (oxidation dye intermediate) | 1.0 g | 1.0 g |
| Diaminophenoxyethanol | 0.05 g | 0.05 g |
| Meta-aminophenol | 0.1 g | 0.1 g |
| Surfactant (Nippon Shokubai, Softanol 90) | 0.50 g | 0.50 g |

TABLE 1-continued

| Ingredients | Liquid hair dye A | Liquid hair dye B |
|---|---|---|
| Oxidation enzymes (Laccase, derived from *Myceliophthora thermophila*) (*1) | 500 U | 500 U |
| Thickener (Dainippon Pharmaceutical, Echo Gum T) | 0.25 g | 1.0 g |
| $NaH_2PO_4 \cdot 12H_2O$ | 1.8 g | 1.8 g |
| 95° Ethanol | 10 g | 10 g |
| 1,3-Butylene glycol | 5 g | 5 g |
| Purified water | balance | Balance |
| Total | 100 g | 100 g |
| Viscosity | 800 mPa · s | 12000 mPa · s |

It should be noted that the enzyme activity (U) of (*1) in Table 1 was measured according to the following method.

Reaction solution (3 mL) containing 1 mM of TDA, 1 mM of resorcin, 25 mM of sodium phosphate buffer (pH: 7), and enzymes was prepared, the increase of light absorbance (506 nm) in the reaction that produced the coloring matter was measured with a spectrophotometer for 1 to 30 minutes at 25° C. in a 1-cm-thick cell, and the enzyme activity (U) was calculated from the change in light absorbance (Abs) at 506 nm during a suitable five-minute period in accordance with the following formula.

Enzyme activity $(U)=(Abs \times 3/0.915)/5$ (2) Discharge Experiment

The change in pressure inside the container from discharge initiation to discharge completion, the discharge velocity, and the specific volume of the foam (foam-type hair dye volume/foam-type hair dye weight) were measured in the case of forming a foam-type hair dye by discharging liquid hair dye with the foam-type hair dye discharge apparatus turned upside down.

As an example of the measuring method for specific volume of the foam, about 50 mL of foam-type hair dye was discharged from the foam-type hair dye discharge apparatus into a measuring cylinder. The volume of the discharged foam-type hair dye and the increased weight of the measuring cylinder due to the discharge were measured thereafter, and the specific volume of the foam was calculated. The results are shown in Table 2.

(3) Hair Dyeing Performance Test

Foam-type hair dye formed by discharging 1 g of liquid hair dye was occasionally collected between discharge initiation and discharge completion when the foam-type hair dye was formed by discharging liquid hair dye with the foam-type hair dye discharge apparatus turned upside down. The obtained foam-type hair dye was applied to a bundle of pre-washed goat hair (about 1 g) having a length of 10 cm, and the hair was dyed at a constant temperature of 30° C. for 30 minutes, washed in water for 30 seconds at 40° C., washed for 15 seconds with a commercially available shampoo, washed in water for 30 seconds at 40° C., rinsed for 15 seconds with commercial plain type rinse, and dried with a dryer using cool air.

After dyeing, the L, a, and b values of the dried goat hair were measured using a color-difference meter (Minolta, Color Difference Meter CR200); mean values of $\Delta L$, $\Delta a$, and $\Delta b$ were found as differences in relation to the L, a, and b values before dyeing; and the color difference $\Delta E$ was thereby calculated.

In order to provide a comparison, goat hair was dyed by directly applying 1 g of liquid hair dye A or B without using the foam-type hair dye discharge apparatus, and the color difference ΔE was calculated in the same manner as that described above. These results are shown in Table 2.

TABLE 2

|  | Example 1 | | Comp. Ex. |
|---|---|---|---|
| Jetting orifice diameter (mm) | 0.4 | 0.5 | 0.6 |
| Pressure change (MPa, maximum to minimum) | 8 to 2.5 | 8 to 2.5 | 8 to 1.8 |
| Specific volume of foam (mL/g, maximum to minimum) | 2.0 to 1.8 | 2.0 to 1.4 | 2.3 to 1.2 |
| Discharge velocity (g/5 sec, maximum to minimum) | 11 to 8 | 22 to 10 | 28 to 10 |
| Dyeing performance (ΔE, maximum to minimum) | | | |
| Hair dye A | 41 to 39 | 40 to 39 | 40 to 38 | 36 |
| Hair dye B | 40 to 38 | 41 to 38 | 41 to 39 | 36 |

From the results in Table 2, the foam-type hair dye discharge apparatus of the present invention is clearly capable of converting liquid hair dye into foam by blending air throughout the process even if pressure within the container changes in the interval between discharge initiation and discharge completion, and even if discharge velocity changes.

It is also clear that dyeing performance is improved by dyeing with liquid hair dye in a foam form.

Example 2

In the foam-type hair dye discharge apparatus 1A shown in FIG. 1A, a double container that comprised an outer container composed of aluminum and an inner bag composed of polyethylene served as the container main body 2, the hole diameter of the jetting orifice 6 was set to 0.5 mm, liquid hair dye C or D containing an air oxidation dye shown in Table 3 was filled into the inner bag, and nitrogen gas was filled to 8 MPa (gage pressure) between the outer container and the inner bag.

Foam-type hair dye (specific volume of about 2 mL/g) was obtained by discharging each of liquid hair dyes C and D from the foam-type hair dye discharge apparatus, and a bundle of gray hair (1 g) was coated with 1 g thereof and dyed at a constant temperature of 30° C. for 15 minutes. The hair was then sequentially washed with water, shampooed, rinsed, and dried. As a result, gray hair was successfully concealed by performing the dyeing process once when the liquid hair dye C was used, and by repeating the dyeing process five times when the liquid hair dye D was used, and it was confirmed that good dyeing performance can be obtained with either dye.

TABLE 3

| Ingredients (wt %) | Hair dye C | Hair dye D |
|---|---|---|
| 5,6-Dihydroxyindoline hydrobromate | 1.0 | — |
| 5,6-Dihydroxyindoline-2-carboxylate hydrochloride | — | 0.3 |
| Monoethanolamine | 3.1 | — |
| Guanidine carbonate | — | 1.4 |
| Ethanol | 10 | 30 |
| Surfactant (Nippon Shokubai, Softanol 90) | 0.1 | 0.1 |
| Xanthan gum | 1 | 1 |

TABLE 3-continued

| Ingredients (wt %) | Hair dye C | Hair dye D |
|---|---|---|
| 10 wt % sulfuric acid | Appropriate amount | Appropriate amount |
| Purified water | balance | Balance |
| pH | 10.5 | 9.5 |
| Viscosity (mPa · s, B-type viscometer, room temperature) | 8700 | 8000 |

Example 3

Liquid hair dye E containing the direct dyes shown in Table 4 was prepared, and the resulting liquid hair dye E and a propellant (nitrogen) were filled into the container main body (volume: about 0.2 L) of the foam-type hair dye discharge apparatus 1A of FIG. 1A in the same manner as in Example 1 to obtain a foam-type hair dye discharge apparatus (hole diameter of jetting orifice 6: 0.5 mm).

The handling characteristics and lack of irregular coloring of the foam-type hair dye discharge apparatus was investigated with ten gray-haired subjects. In this case, an application method was used whereby liquid hair dye was discharged from a foam-type hair dye discharge apparatus turned upside down in the manner shown in FIG. 2, and the resulting foam-type hair dye was taken up by a commercial brush or comb and applied to head hair.

As a result, the average application time was 10 minutes or less, and was shorter in comparison with an average application time of 15 minutes or more in the case of directly applying liquid hair dye E with a brush or comb. It is clear that using the foam-type hair dye discharge apparatus of the present invention facilitates the spreading and application of the dye because of the presence of foam, and the handling characteristics of the foam-type hair dye discharge apparatus of the present invention are therefore improved.

When the lack of irregular coloring after dyeing was evaluated by each subject, seven subjects responded that there was no irregular coloring, and three subjects responded that there was substantially no irregular coloring. It was confirmed that the foam-type hair dye discharge apparatus of the present invention has superior application characteristics without irregular coloring.

TABLE 4

| Ingredients (wt %) | Hair dye E |
|---|---|
| Lactic acid | 3 |
| NaOH | Appropriate amount |
| Benzyl alcohol | 10 |
| Ethanol | 10 |
| Surfactant (Nippon Shokubai, Softanol 90) | 0.5 |
| Tactile improvers (silicones) | Trace amount |
| Thickener (hydroxypropyl xanthan gum) | 1.5 |
| Dyes: Orange 205 | 0.35 |
| Black 401 | 0.04 |
| Red 227 | 0.03 |
| Purified water | Balance |
| Viscosity (mPa · s, B-type viscometer, room temperature) | 20000 |

Handling is improved when hair dye is applied to hair by the foam-type hair dye discharge apparatus of the present invention, wherein liquid hair dye is converted to foam by blending air from outside the container into jet flow of the liquid hair dye and allowing the resulting material to strike the liquid reservoir member. In addition, the hair dye is easier to store because liquid hair dye can be sealed and stored in isolation from outside air when the hair dye is not in use.

The foam-type hair dye discharge apparatus of the present invention, which uses a double aerosol container wherein undiluted solution and compressed gas for jetting the undiluted solution foam are individually sealed and stored, the compressed gas is jetted during the discharge of the undiluted solution, and these components are mixed and discharged in foam form, may be applied to cases where an undiluted solution and a compressed gas cannot be stored in mixed form. In particular, when a liquid hair dye containing an air-oxidation dye is filled as an undiluted solution, and compressed air is used as compressed gas, good dyeing performance can be achieved because the air-oxidation dye and air are discharged as an adequately mixed foam.

The entire disclosure of the specification, claims, summary and drawings of Japanese Patent Application Nos. 2002-058579 and 2002-111273, filed on Mar. 5, 2002 and Apr. 12, 2002 are respectively, hereby incorporated by reference.

What is claimed is:

1. A foam hair dye, comprising:
a liquid hair dye that contains at least one oxidation dye, at least one surfactant, and at least one thickener, and a gas that is blended into a jet flow of said oxidation liquid hair dye, wherein said gas is air from outside the container;
wherein the hair dye is an undiluted solution; and
wherein the specific volume of the foam is 1.2 to 5 mL/g.

2. The foam hair dye of claim 1, wherein the specific volume of the foam is 1.2 to 2.3 mL/g.

3. The foam hair dye of claim 1, wherein the liquid hair dye comprises from 0.01 to 5 wt. % of the dye based on the total weight of the liquid hair dye.

4. The foam hair dye of claim 1, wherein the liquid hair dye further comprises a surfactant.

5. The hair dye of claim 4, wherein the surfactant is present in an amount of from 0.01 to 5 wt. % based on the total weight of the liquid hair dye.

6. The foam hair dye of claim 1, wherein the thickener is at least one selected from the group consisting of hydroxyethyl cellulose, an ether of a hydroxyethyl cellulose, an ether of a glycidyl trimethylammonium chloride, methyl cellulose, carboxymethyl cellulose, xanthane gum, guar gum, polyvinylpyrrolidone, crosslinked polyacrylic acid, a salt of a crosslinked polyacrylic acid, polyacrylic acid, a salt of polyacrylic acid, and a polyacrylamide.

7. The foam hair dye of claim 1, wherein the specific volume of the foam hair dye is from 1.3 to 3 mL/g.

8. The foam hair dye of claim 1, comprising toluene-2,5-diamine, diamino phenoxy ethanol, meta-aminophenol, a surfactant, an oxidation enzyme, ethanol, 1,3-butyleneglycol and water.

9. The foam hair dye of claim 8, wherein the oxidation enzyme is a laccase.

10. An application method for foam hair dye, comprising blending air from outside a container with a jet flow of a liquid hair dye by jetting the liquid hair dye containing a dye, surfactant, and thickener from one or a plurality of jetting orifices of a discharge container to a liquid reservoir member disposed opposite the jetting orifices;
forming a foam hair dye in the liquid reservoir member; and
applying the foam hair dye to hair;
wherein the liquid hair dye is not diluted.

11. The method of claim 10, wherein the liquid hair dye comprises an oxidation dye and the liquid hair dye is jetted in undiluted form.

12. The method of claim 10, wherein the liquid hair dye further comprises an enzyme.

13. A foam hair dye discharge apparatus, comprising:
a container main body in which liquid hair dye containing an oxidation dye, surfactant, and thickener is stored;
at least one jetting orifice configured to jet the liquid hair dye from the container main body; and
a liquid reservoir member disposed opposite the jetting orifices,
wherein air from outside the container is blended with the jet flow of liquid hair dye jetted from the jetting orifices toward the liquid reservoir member, and a foam hair dye is formed in the liquid reservoir member;
wherein the liquid hair dye is not diluted.

14. A foam hair dye, comprising:
a liquid hair dye and a gas,
wherein the foam hair dye is obtained by mixing a jet flow of the liquid hair dye with the gas,
wherein the gas is air and the liquid hair dye is free of a propellant,
wherein the liquid hair dye comprises at least one dye, at least one surfactant and at least one thickener, and
wherein the foam hair dye has a specific volume of from 1.2 to 5 mL/g.

* * * * *